United States Patent
Dolcetti et al.

(10) Patent No.: US 8,512,703 B2
(45) Date of Patent: Aug. 20, 2013

(54) IDIOTYPIC VACCINE

(75) Inventors: Riccardo Dolcetti, Cordenons (IT); Massimo Guidoboni, Castellina in Chianti (IT); Valli De Re, Sacile (IT); Daniela Gasparotto, Azzano Decimo (IT); Sonia Castiglioni, Milan (IT); Maria Luisa Nolli, Milan (IT)

(73) Assignee: Areta International S.R.L., Milan (IT)

( * ) Notice: Subject to any disclaimer, the term of this patent is extended or adjusted under 35 U.S.C. 154(b) by 552 days.

(21) Appl. No.: 12/670,949

(22) PCT Filed: Jul. 24, 2008

(86) PCT No.: PCT/IB2008/001936
§ 371 (c)(1),
(2), (4) Date: Mar. 23, 2010

(87) PCT Pub. No.: WO2009/016456
PCT Pub. Date: Feb. 5, 2009

(65) Prior Publication Data
US 2010/0310586 A1     Dec. 9, 2010

(30) Foreign Application Priority Data
Jul. 27, 2007   (IT) .............................. MI2007A1522

(51) Int. Cl.
*C12P 21/00* (2006.01)
*C12P 21/02* (2006.01)
*C12P 21/04* (2006.01)
*A61K 39/395* (2006.01)
*A61K 39/00* (2006.01)

(52) U.S. Cl.
USPC .................... 424/133.1; 424/130.1; 435/69.1; 435/71.1; 435/71.2

(58) Field of Classification Search
None
See application file for complete search history.

(56) References Cited

U.S. PATENT DOCUMENTS
2002/0115846 A1   8/2002   Yu et al.

OTHER PUBLICATIONS

GI:51949939. Immunoglobulin kappa light chain variable region, partial [*Homo sapiens*]. Sep. 14, 2004.*

GI:11275922. Immunoglobulin kappa chain, partial [*Homo sapiens*]. Nov. 22, 2000.*

Kwak et al. Induction of Immune Responses in Patients with B-Cell Lymphoma Against the Surface-Immunoglobulin Idiotype Expressed by Their Tumors. The New England Journal of Medicine 1992, vol. 327, No. 17, pp. 1209-1215.*

Hawkins et al. Idiotypic Vaccination Against Human B-Cell Lymphoma. Blood 1994, vol. 83, No. 11, pp. 3279-3288.*

Redfern et al. Phase II Trial of Idiotype Vaccination in Previously Treated Patients with Indolent Non-Hodgkin's Lymphoma Resulting in Durable Clinical Responses. Journal of Clinical Oncology Jul. 1, 2006, vol. 24, No. 19, pp. 3107-3112.*

International Search Report for PCT/IB2008/001936 mailed Jun. 29, 2009.

Written Opinion of the International Searching Authority for PCT/IB2008/001936, mailed Jun. 29, 2009.

De Re, V. et al., "Sequence analysis of the immunoglobulin antigen receptor of hepatitis C virus-associated non-Hodgkin lymphomas suggests that the malignant cells are derived from the rheumatoid factor-producing cells that occur mainly in type II cryoglobulinemia", Blood, vol. 96, No. 10, (Nov. 15, 2000), pp. 3578-3584.

De Re, V. et al., "Pre-Malignant and Malignant Lymphoproliferations in an HCV-Infected Type II Mixed Cryoglobulinemic Patient Are Sequential Phases of an Antigen-Driven Pathological Process", International Journal of Cancer, vol. 87, No. 2, (Jul. 15, 2000), pp. 211-216.

Wen, Y-J et al., "In-Vivo immune responses to idiotypic VH complementarity-determining region 3 peptide vaccination in B-cell non-Hodgkin's lymphoma", British Journal of Haematology, vol. 103, No. 3, (Dec. 1, 1998), pp. 663-668.

Sansonno, D. et al., "Hepatitis C virus, cryoglobulinaemia, and vasculitis: immune complex relations", Lancet Infectious Diseases, vol. 5, No. 4, (Apr. 1, 2005), pp. 227-236.

Vuist, W. et al., "Lymphoma Regression Induced by Monoclonal Anti-Idiotypic Antibodies Correlates With Their Ability to Induce Ig Signal Transduction and Is Not Prevented by Tumor Expression of High Levels of Bcl-2 Protein", Blood, vol. 83, No. 4, (1994), pp. 899-906.

* cited by examiner

*Primary Examiner* — Louise Humphrey
(74) *Attorney, Agent, or Firm* — Nixon & Vanderhye PC

(57) ABSTRACT

The invention concerns the use of recombinant clonotypic immunoglobulins (Ig) as a vaccine in the treatment of HCV-related and non HCV-related lymphoproliferations, in particular the use of recombinant proteins with immunogenic properties derived from protein segments VK3-20 and VK3-15 of Ig light chains derived from patients with lymphoproliferations.

21 Claims, 9 Drawing Sheets

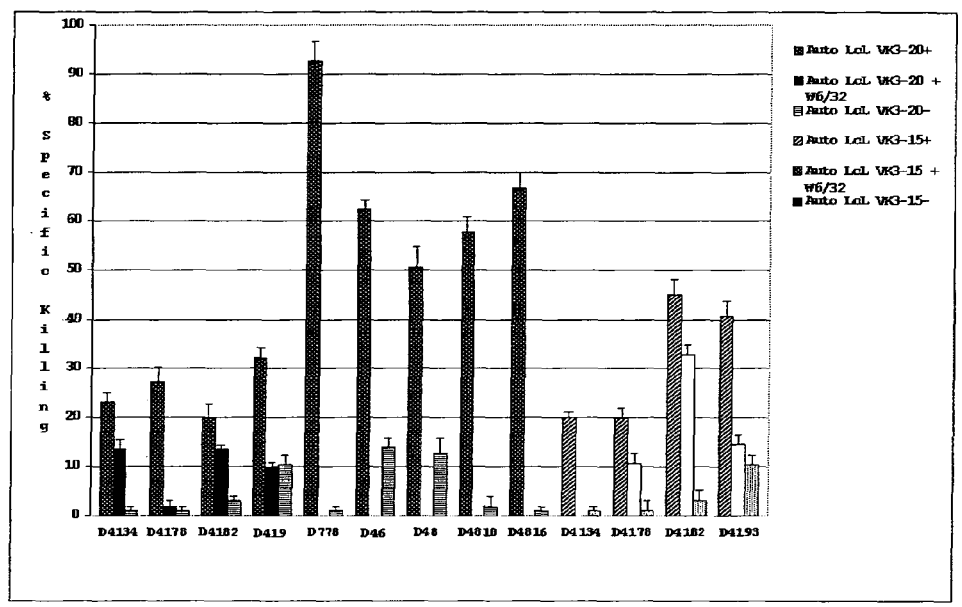
Figure 1 shows the specific cytotoxic activity of polyclonal Cytotoxic T Lymphocyte lines (CTL) sensitized with recombinant immunogenic prot

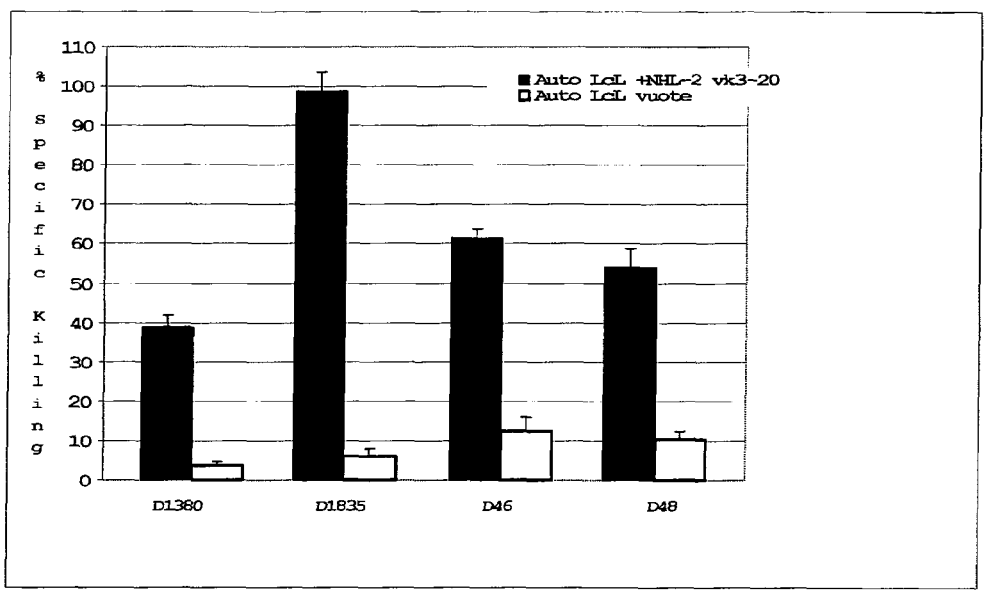
Figure 2 shows the specific cytotoxic activity of polyclonal CTL lines sensitized with recombinant immunogenic protein segments VK3-20 from different patients to check their cross-recognition.

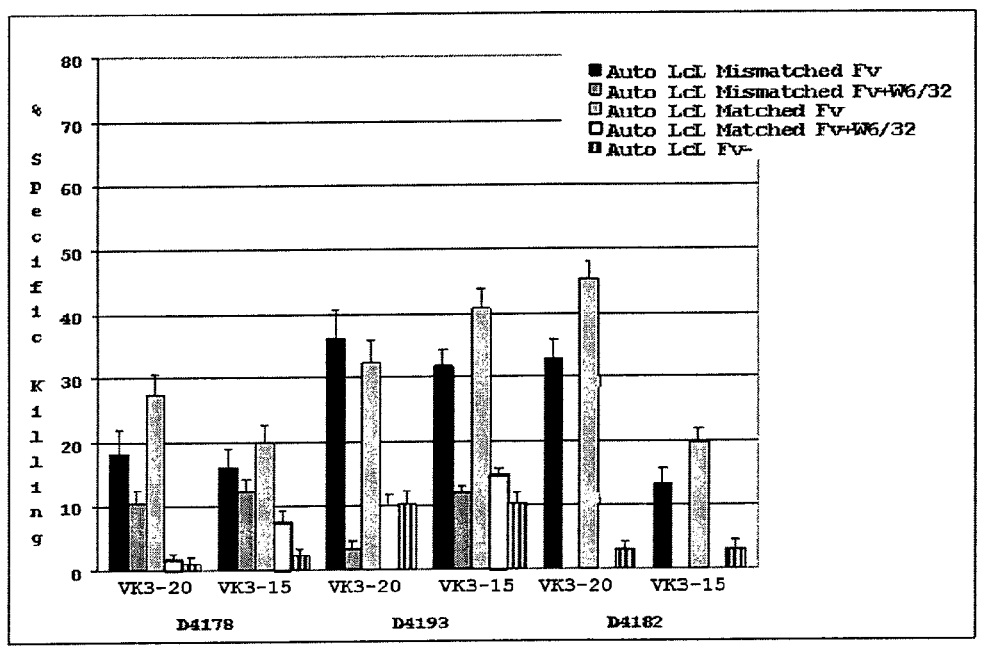
Figure 3 shows the specific cytotoxic activity of polyclonal CTL lines sensitized with recombinant immunogenic protein segments VK3-20 or VK3-15 for the recognition of "matched" or "mismatched" autologous targets.

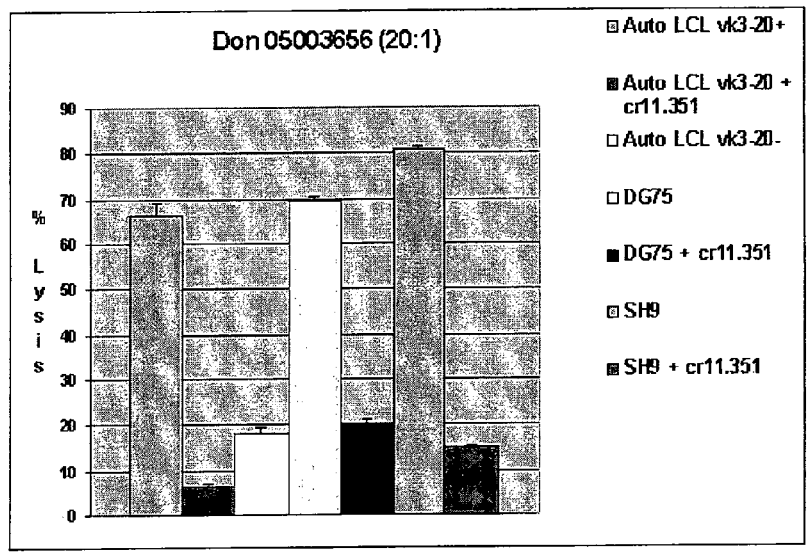
Effectors: VK3-20-specific CTL
Targets: autologous LCL
        DG75 (HLA-A2, VK3-20+)
        SH9 (HLA-A2, VK3-15+)
Figure 4 shows the capability of VK3-20-specific CTL to recognise and kill in HLA Class I-restricted mode both lymphoma B cells (DG75) naturally expressing the protein VK3-20 and a B-lymphoblastoid line (SH9) naturally expressing the molecularly related protein VK3-15.

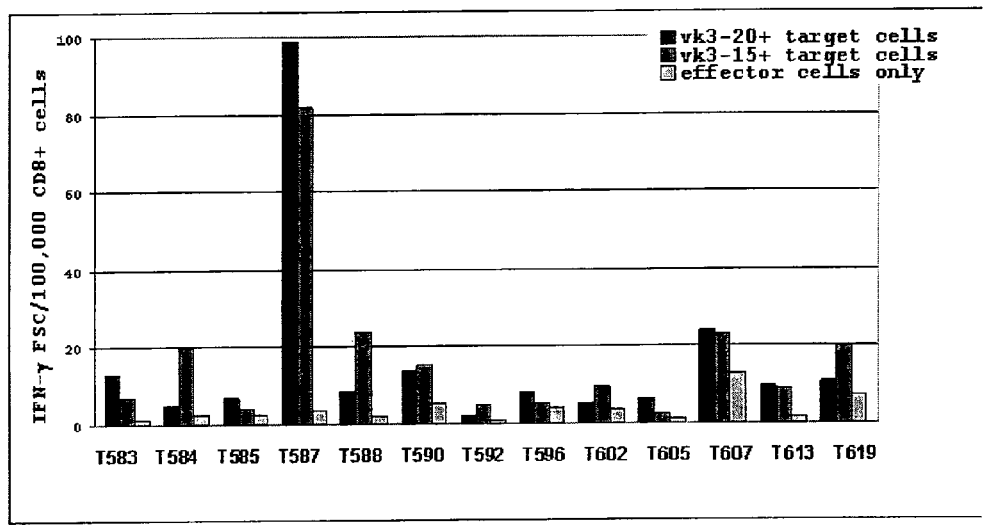
Figure 5 shows the presence of memory-specific responses for VK3-20 or VK3-15 from CD8+ T-lymphocytes in patients with HCV-related lymphomas assessed by INF-γ-ELISPOT assays.

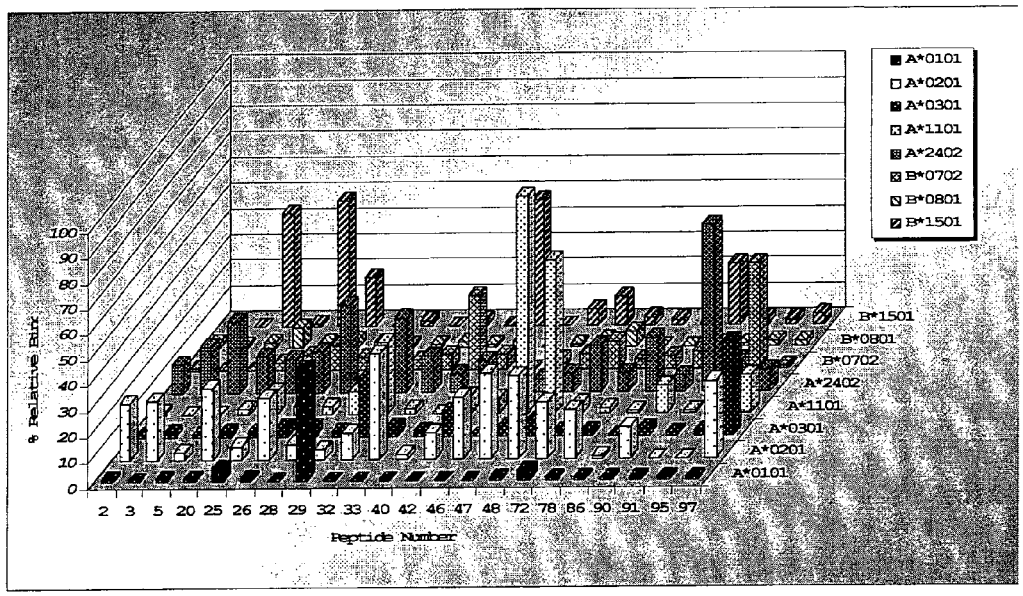
Figure 6 shows the relative percentage of peptide bonds of the protein VK3-20 to 8 different HLA Class I alleles determined using the iTOPIA system.

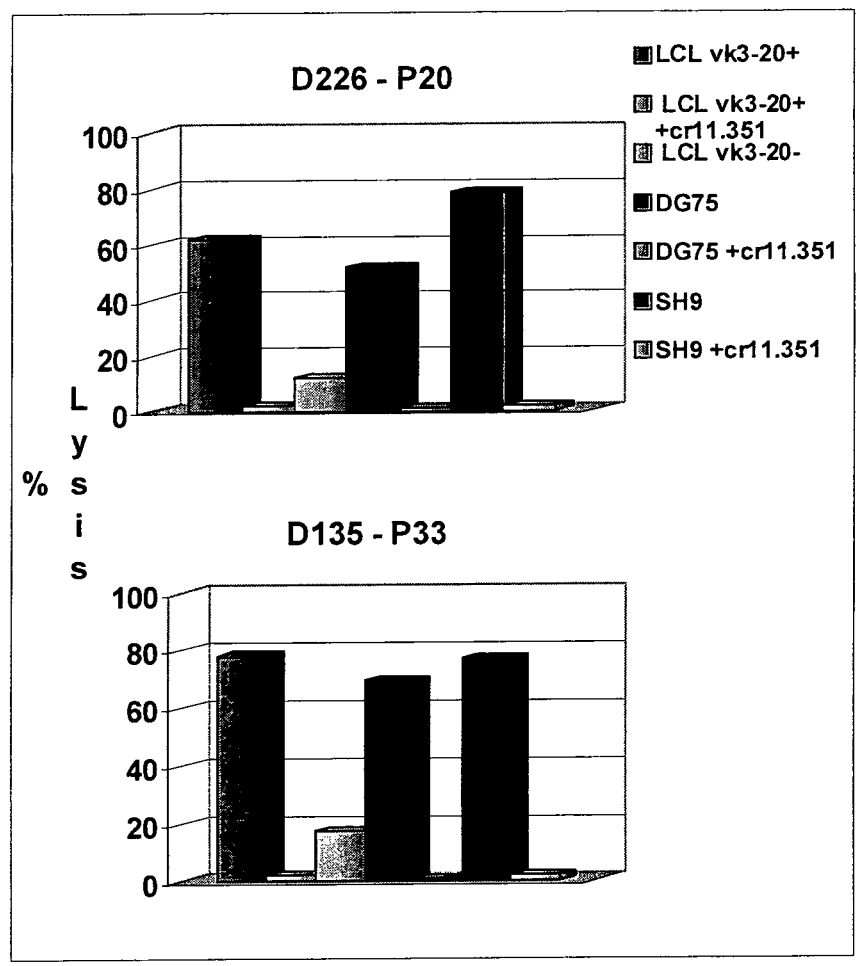
Figure 7 shows the citotoxic activity of specific CTL lines for HLA-A*0201 P20 peptide and P33 peptide. cross-reactive peptide compared to P33 peptide (VK3-20) and VK derived chain.

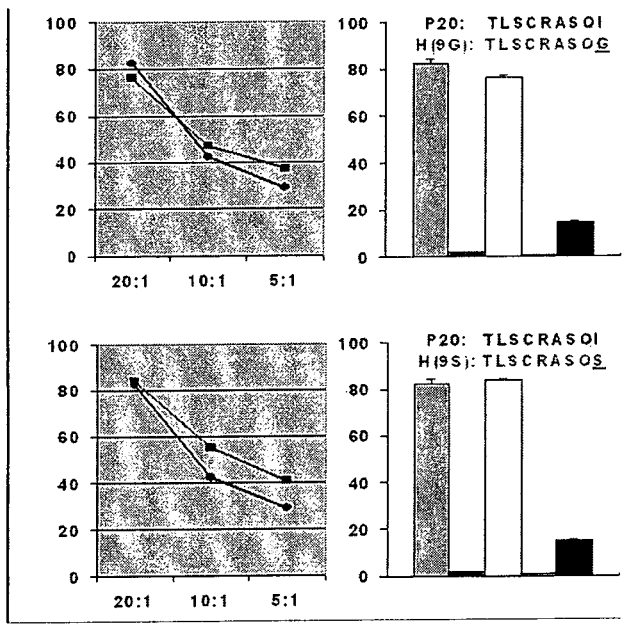
Figure 8 shows the citotoxic activity of specific CTL lines for HLA-A*0201 P20 peptide against cross-reactive peptides present in many VK protein.

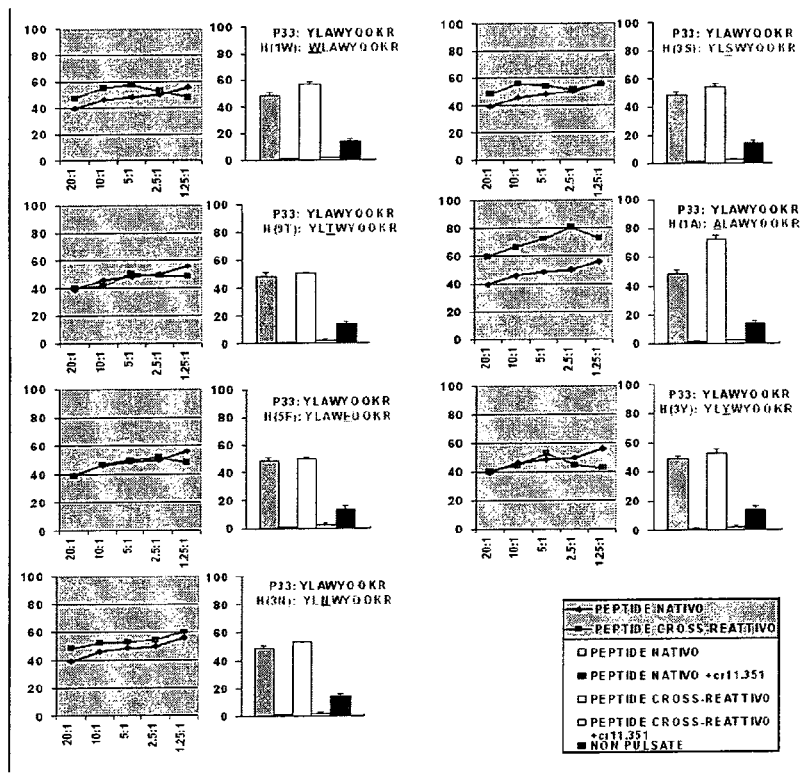
Figure 9 shows the citotoxic activity of specific CTL lines for HLA-A*0201 P33 peptide against cross-reactive peptides present in many VK protein.

IDIOTYPIC VACCINE

This application is the U.S. national phase of International Application No. PCT/IB2008/001936 filed 24 Jul. 2008, which designated the U.S. and claims priority to Italy Application No. MI2007A001522 filed 27 Jul. 2007, the entire contents of each of which are hereby incorporated by reference.

FIELD OF THE INVENTION

The present invention concerns the use of recombinant clonotypic immunoglobulins (Ig) as a vaccine in the treatment of HCV-related and non HCV-related lymphoproliferations. Specifically the present invention provides for the use of recombinant proteins with immunogenic properties derived from protein segments VK3-20 and VK3-15 of Ig light chains derived from patients with lymphoproliferations.

BACKGROUND OF THE INVENTION

Hepatitis C is a form of hepatitis caused by a specific virus (Hepatitis C Virus, HCV). In many cases acute hepatitis C has no symptoms and becomes chronic causing long-term damage to the liver; for example cirrhosis and hepatocellular carcinoma. Other associated symptoms may appear in the presence of hepatitis C such as thyroidism, cryoglobulinemia and some types of glomerulonephritis In particular the term "cryoglobulinemia" refers to the presence in the serum of one or more immunoglobulins (Ig), which precipitate below 37° C. and redissolve on re-warming. Cryoglobulinemia is usually classified into three subgroups: simple cryoglobulinemia (type 1), characterised by the presence of monoclonal Ig, is often associated with haematological diseases and is frequently asymptomatic; mixed cryoglobulinemia or MC (type 2 and type 3) is characterised by the presence of circulating immune-complexes composed of polyclonal IgG, as autoantigens, and of mono-(type 2) or polyclonal (type 3) IgM, as corresponding autoantibodies. MC may be secondary to numerous infections or immunological disorders; when isolated MC may represent a distinct disease, the so-called "essential" MC. Given the striking association (>90%) with HCV infection, the term "essential" is now referred to a minority of MC patients (<5%). HCV may infect the lymphoid tissues and may trigger a mono-polyclonal B-lymphocyte proliferation with different autoantibody production, including the cryoglobulins. MC syndrome is a systemic vasculitis, secondary to the precipitation of circulating immune-complexes and complement in small-sized vessels Clinically, it is characterized by different organ involvement: purpura, skin ulcers, hepatitis, glomerulonephritis, peripheral neuropathy, and/or widespread vasculitis. Some patients may develop a malignancy, usually as late complication, in particular, B-cell non-Hodgkin lymphoma (10%), hepatocellular carcinoma (<5%), or thyroid cancer (<1%).

The first-line treatment of MC should be directed to HCV eradication by interferon and ribavirin; however, this treatment is often unable to eradicate the virus and it may be complicated by important side effects (neuropathy, thyroiditis, etc.). Pathogenetic treatments (plasmapheresis, immunosuppressors, and/or corticosteroids) should be tailored for each patient according to the activity and severity of clinical manifestations. The use of interferon therapy in HCV-related cryoglobulinemic syndrome is based on the assumption that the B-lymphocyte proliferation is virus-dependent and therefore potentially responsive to viral load reduction; so it is not a therapy aimed at the treatment of lymphoproliferations. This therapy with interferon or pegylated-interferon, suitable for increasing the plasmatic half-life of the drug, is also associated with toxicity and side-effects such as: irritability, emotional instability, states of depression, sleep disorders, states of fear, maniacal states, cognition disorders (memory, concentration), confusional states.

It is therefore necessary to find an alternative prophylactic and/or therapeutic therapy for the treatment of the lymphoproliferations briefly described here.

Vaccination with idiotypic Ig has been used for the treatment of B-cell non-Hodgkin lymphoma (NHL), but the notable complexity and high costs involved in producing idiotypic Ig for each patient place significant limits on the application of this vaccination strategy for a large population of subjects.

SUMMARY OF THE INVENTION

The object of the present invention is to supply a new vaccine for lymphoproliferative pathologies, which overcomes the limits and inconveniences of the techniques used up till now and which is applicable to numerically significant groups of patients.

Another object of the present invention is to supply a process for the identification, isolation and assessment of the immunogenicity of the protein segments suitable for the preparation of said vaccine.

A further object is to supply a process for the preparation of the protein segments that constitute said vaccine.

DESCRIPTION OF PREFERRED EMBODIMENTS

These and other aims are achieved with the use of clonotypic recombinant immunogenic segments in the treatment of HCV- and non HCV-related lymphoproliferations.

So, according to one of its aspects, the invention concerns a vaccine comprising at least one recombinant immunogenic protein segment chosen between VK3-20 and VK3-15, destined for the treatment and/or prophylaxis of lymphoproliferative pathologies.

According to another of its aspects, the invention concerns the use of a recombinant immunogenic protein segment chosen between VK3-20, VK3-15 and mixtures thereof.

For the use according to the invention, the recombinant immunogenic protein segment or segments chosen between VK3-20, VK3-15 and mixtures of the same, is or are alternatively combined with another protein portion or reagent for the preparation of a vaccine for the treatment and/or prophylaxis of lymphoproliferative pathologies.

According to another of its aspects, the invention concerns the use of a vaccine comprising both recombinant immunogenic protein segments VK3-20 and VK3-15 for the preparation of a medicament for lymphoproliferative pathologies.

In particular the term "recombinant immunogenic protein segments" is intended to refer to protein parts obtained through the recombinant DNA technique and provided with immunogenic activity, i.e. able to induce an immune response.

The terms VK3-20 and VK3-15 refer to variable regions of the Ig κ type light chain.

The nucleotide sequences of the coding genes for VK3-20 and VK3-15 are in the NCBI database with accession number: AF303897/AAG33824 for VK3-20 and AAU14891/AY704914 for VK3-15.

According to another of its aspects, the present invention concerns the isolation, characterisation, production and purification of the recombinant clonotypic segments VK3-20 and VK3-15.

According to an embodiment of the invention, the process for the production, implementation and purification of the recombinant clonotypic segments VK3-20 and VK3-15 comprises the following passages:

1) insertion of the nucleotide sequences that encoding for said proteins in a suitable expression vector;
2) inoculation in an appropriate culture medium;
3) fermentation, according to known techniques; and
4) purification of the fragments.

According to a preferred embodiment of the present invention, the production process is characterised in that at least two of the passages from (1) to (4) are carried out according to the passages from (1') to (4'):

1') insertion of said sequences in the expression vector pET26b, to form the recombinant bacterial strain pET26b/VK3-20/VK3-15;
2') inoculation of a bacterial aliquote of 1% in volume;
3') fermentation using as culture medium SB buffered with a phosphate buffer and adding glucose or Isopropyl Thiogalactoside (IPTG);
4') purification by ion exchange chromatography.

According to the present invention, the term "pET26b/VK3-20/VK3-15" refers to the engineered expression vector pET26b containing alternatively the nucleotide sequence that encodes for one of the two recombinant idiotypic protein chains VK3-20 and VK3-15.

According to the present invention the identification and quantification alternatively of the segments of the recombinant idiotypic protein chains VK3-20 and VK3-15 is performed with monoclonal antibodies (mAb) directed against the VK regions.

According to the present invention the term mAb refers to a homogeneous population of antibodies produced by a cell clone (hybridoma) obtained by the fusion of immunoproductive cells with tumour cells, usually malignant myeloma cells, with specificity for only one epitope of the immunogenic antigen.

According to a particularly preferred embodiment, the invention process comprises all the passages from (1') to (4').

The improved and optimized process produces numerous advantages with respect to the known processes; in fact it allows to:
accelerate the grown of the recombinant bacterial cultures and to increase their biomass up to 50%;
increase the process yield;
decrease production times and costs; and
simplify, reproduce and industrial scale up according to good manufacturing practice (GMP).

According to another preferred embodiment of the invention, the fermentation of the bacterial strain contemplates that it is kept in culture at 37° C. for 8-12 hours, for example overnight.

Also according to a preferred embodiment of the invention, the purification of the recombinant idiotypic protein chains, from the culture medium or from the bacterial periplasmic space, involves a step on an ion exchange column, for example Q Sepharose FF (Amersham-GE) and S Sepharose FF (Amersham-GE).

Details on the process of the invention are given in the experimental part of the present description.

It has been observed that the recombinant immunogenic segment VK3-20 is able to recognise 22 immunogenic epitopes, as indicated in Example 5 of the experimental part of this description.

According to another of its aspects, the present invention concerns any protein segment able to recognise at least one of the 22 immunogenic epitopes identified by the protein segment VK3-20, preferably more than one epitope, advantageously all 22 epitopes.

The vaccine of the present invention is used in HCV- and non HCV-related lymphoproliferations. It has in fact been observed that the cytotoxic responses stimulated by a prototypic light chain VK3-20, derived from an HCV-related lymphoma, present a significant cross-reactivity even against to an idiotypic VK protein codified from the same gene but derived from a different patient, and for this reason the vaccine prepared according to the invention is efficacious and may be administered to numerically representative patient populations as treatment and/or prophylaxis in lymphoproliferative pathologies. Non HCV-related lymphoproliferations can therefore be treated, such as for example follicular lymphoma (FL), chronic lymphocyte leukaemia (CLL), lymphomas of the mucosa-associated lymphoid tissue (MALT) and lymphomas associated with autoimmunity such as rheumatoid arthritis, Sjögren's syndrome.

For its therapeutic and/or prophylactic use, the vaccine of the invention is preferably administered in suitable pharmaceutical compositions.

The invention also concerns the use of any protein segment able to recognise at least one of the 22 immunogenic epitopes identified by the protein segment VK3-20, preferably more than one epitope, advantageously all 22 epitopes, for the preparation of a vaccine for the treatment and/or prophylaxis of HCV- and non HCV-related lymphoproliferations.

The pharmaceutical compositions containing said vaccine represent a further aspect of the invention.

In the pharmaceutical compositions of the present invention for oral, subcutaneous, intravenous, transdermic or topic administration, the protein segments are preferably administered in a single dose, as a mixture with the classic excipients or pharmaceutically acceptable vehicles. The used dose can vary according to age, weight and health conditions of the patient, or according to the pathological severity level and to the route of administration. (A range is preferred. For example from 0.1 to 1 mg, preferably from 0.3 to 0.7 mg, for example 0.5 mg per dose unit).

The vaccine and/or the pharmaceutical composition of the invention may eventually be administered in combination with other drugs used in therapy, for example with sargramostim (GM-CSF, 50 µg/m$^2$/dose) and/or recombinant IFN-α2a (1,000,000 UI/m$^2$/dose).

According to another of its aspects the invention comprises a kit for the treatment and/or prophylaxis of lymphoproliferative pathologies, which comprises the pharmaceutical composition of the invention in and/or sargramostim and/or recombinant IFN-α2a.

The kit of the invention preferably comprises the pharmaceutical composition of the invention in the form of a dose unit comprising the active principle in an amount of 0.5 mg and/or sargramostim (GM-CSF, 50 µg/m$^2$/dose) and/or recombinant IFN-α2a (1.000.000 UI/m$^2$/dose).

BRIEF DESCRIPTION OF THE DRAWINGS

The invention will be illustrated by means of non limiting examples, related to the enclosed figures, that are supplied solely for indicative and non limiting purposes, where:

FIG. 1 shows the specific cytotoxic activity of polyclonal Cytotoxic T Lymphocyte lines (CTL) sensitized with recombinant immunogenic protein segments VK3-20 and VK3-15;

FIG. 2 shows the specific cytotoxic activity of polyclonal CTL lines sensitized with recombinant immunogenic protein segments VK3-20 from different patients to check their cross-recognition;

FIG. 3 shows the specific cytotoxic activity of polyclonal CTL lines sensitized with recombinant immunogenic protein segments VK3-20 or VK3-15 for the recognition of "matched" or "mismatched" autologous targets;

FIG. 4 shows the capability of VK3-20-specific CTL to recognise and kill in HLA Class I-restricted mode both lymphoma B cells (DG75) naturally expressing the protein VK3-20 and a B-lymphoblastoid line (SHP) naturally expressing the molecularly related protein VK3-15.

FIG. 5 shows the presence of memory-specific responses for VK3-20 or VK3-15 from CD8+ T-lymphocytes in patients with HCV-related lymphomas assessed by INF-γ-ELISPOT assays.

FIG. 6 shows the relative percentage of peptide bonds of the protein VK3-20 to 8 different HLA Class I alleles determined using the iTOPIA system.

FIG. 7 shows the citotoxic activity of specific CTL lines for HLA-A*0201 P20 peptide and P33 peptide. cross-reactive peptide compared to P33 peptide (VK3-20) and VK derived chain.

FIG. 8 shows the cytotoxic activity of specific CTL lines for HLA-A*0201 P20 peptide (SEQ ID NO: 6) against cross-reactive peptides (SEQ ID NOS 26 and 25, respectively, in order of appearance) present in many VK protein.

FIG. 9 shows the cytotoxic activity of specific CTL lines for HLA-A*0201 P33 peptide SEQ ID NO: 27) against cross-reactive peptides (SEQ ID NOS 31, 30, 28, 32, 29 and 33-34, respectively, in order of appearance) present in many VK protein.

EXAMPLE 1

Isolation, Preparation, In Vitro Characterisation of Recombinant Clonotypic Ig The VH and VK regions of six HCV patients infected with type II mixed cryoglobulinemia and concomitant NHL-B were inserted and reproduced in vitro and the single-filament proteins (ScFv) deriving from these sequences were produced and purified by affinity.

Only the proteins derived from the VK chain of two patients, VK3-20 (VK-gal) and VK3-15 (VK-gent), were further immunologically characterised in vitro. The DNA was extracted respectively from the tumour cells obtained from a hepatic biopsy and from bone marrow cells, both tissues were involved by a low-malignity non-Hodgkin lymphoma of a lymphoplasmacytic-lymphoplasmacytoid type according to the Kiel classification. In both cases the VK region was amplified as reported previously (De Re V, and col. Blood. 2000; 96:3578-84). The genes that form the variable regions of the immunoglobulin light chain are: VK3-20/JKI*01 and VK3-15/JK1*01. The VK sequences were subsequently cloned and expressed as a single fragment. For this purpose, the PCR products were recovered from the agarose gel, digested with the restriction enzymes BamHI and XhoI, and linked in the restriction site BamHI-XhoI of the plasmidic vector pET26b (Novagen, Madison, Wis., United States) to form the expression plasmids pET26b/VK3-20 and pET26b/VK3-15. The downstream primer FL7 (5'-CGG GAT CCG GAA ATT GTG TTG ACG-3') (SEQ ID NO: 1) presents a restriction site for the enzyme BamHI and FL5 primer (5'CCG CTC GAG TCA TTT GAT TTC CAC C-3') SEQ ID NO: 2) presents the restriction site XhoI at 3' end.

Cultures of polyclonal Cytotoxic T Lymphocytes (CTL) were obtained by stimulation of peripheral blood mononucleate cells (PBMC) from thirteen healthy donors not related to one another, genotyped according to the histocompatibility system, with autologous dendritic cells pulsed with the idiotypic proteins VK3-20 and VK3-15. In this way nine lines of CTL stimulated with VK3-20 and four lines of CTL stimulated with VK3-15 were obtained. To assess immunogenicity in vitro, cytotoxicity tests were performed using radioisotope ($^{51}$Cr) and non radioactive method (calcein release). Another test of the in vitro immunogenicity of these proteins, aimed to assessing the antigen specificity of the induced immune responses, was performed assessing the inhibition percentage of the specific cytotoxic activity in the presence of the commercially available antibody W6/32, obtaining the demonstration that the used mechanism is HLC class I-restricted (FIG. 1).

EXAMPLE 2

Cross-Recognition of Recombinant Idiotypic Proteins

It has been observed that the cytotoxic responses stimulated by a prototypical light chain VK3-20, derived from an HCV-related lymphoma, present a cross-reactivity even with regard to an idiotypic VK protein codified from the same gene (VK3-20) but derived from the lymphoma of a different patient (FIG. 2). The data in FIG. 2, obtained from four unrelated donors and distinguished by different HLA class I haplotypes, show how the cytotoxic immune responses induced by a recombinant prototype protein VK3-20 have a significant immunotherapeutic potential also in non related patients affected by lymphomas expressing idiotypic immunoglobulins including light chains VK3-20.

EXAMPLE 3

Assessment of the Cross-Reactivity of VK3-20- and VK3-15-Specific CTL

Further experiments were carried out to assess the capability of VK3-20- and VK3-15-specific CTL to recognise and kill both autologous matched targets, or rather charged with the corresponding protein used for the generation of the CTL, and autologous mismatched targets, or rather charged with the molecularly related protein VK3. In the considered three donors, as shown in FIG. 3, the VK3-20- and VK3-15-specific CTL are able to kill with Class I-restricted mode even targets charged respectively with VK3-15 and VK3-20 (mismatched targets). In fact the two VK3 proteins possess a sequence homology greater than 80% and this justifies their cross-reactivity. This provides the rational for using these recombinant proteins as vaccines for the treatment and prevention of lymphoproliferations expressing molecularly related idiotypes. It has also been shown how VK3-20-specific CTL recognise and kill in Class I-restricted mode both lymphoma B cells (DG75) naturally expressing the protein VK3-20 and a B-lymphoblastoid line (SH9) naturally expressing the molecularly related protein VK3-15 (FIG. 4). This indicates that VK3-20 and VK3-15 expressed by lymphoproliferation B cells are naturally processed and physiologically produce immunogenic epitopes able to mediate cellular-mediate immune responses of potential clinical value.

EXAMPLE 4

Identification of Memory Responses

In order to identify specific memory cells for the idiotypic Ig selected in patients affected by lymphoid neoplasms, ELISPOT analyses were carried out, based on the identification of CD8+ T-lymphocytes secreting interferon-γ. Said analyses show, FIG. 5, the presence of specific memory responses for VK3-15 and VK3-20 in patients affected by VK+ lymphoma. Assays with the ELISPOT method were carried out at 48 hours on PBMC of 13 patients with HCV-related lymphoma, using as cells presenting antigen autologous monocytes charged with the selected recombinant proteins and CD8+ T-lymphocytes as "responder" cells.

EXAMPLE 5

Identification and Validation of Immunogenic Epitopes

In order to identify the VK3-20 peptides able to bind the most common HLA class I alleles, analyses were carried out of the VH and VL regions obtained from clonotypic Ig of HCV-associated lymphoproliferations with computerised methods for predicting the epitopes (Syfpeithi, Net-MHC, Bimas). For the HLA-A*0201 allele only, 35 potential epitopes able to bind this restriction element were identified. In order to identify and validate the immunogenic epitopes of the protein VK3-20, the iTopia™ high-throughput Epitope Discovery System was used (Beckman Coulter). The immunogenic epitopes of the protein VK3-20 were then identified. Through a series of ELISA-like tests of the binding, not binding and affinity of the peptides with HLA molecules in recombinant form, a library of 100 nonamers was analysed, overlapped of one amino acid, derived from VK3-20 protein. Then 22 peptides were identified with moderate binding capabilities each one of 7 different HLA-A and -B alleles (FIG. 6 and Table 1). It was also demonstrated that CTLs induced in different donors with the protein VK3-20 recognise and kill in A2-restricted mode both targets charged with A*0201 peptides and the SJ9 lymphoblastoid line naturally expressing the protein VK3-15. This further confirms the cross-reactivity of the immune responses induced by epitopes of the protein VK3-20.

TABLE 1

(Table 1 discloses SEQ ID NOS 3-24, respectively, in order of appearance)

Bond results

| Peptide | | Class I HLA molecules | | | | | | |
|---|---|---|---|---|---|---|---|---|
| N° | Sequence | A*0101 | A*0201 | A*0301 | A*1101 | A*2402 | B*0702 | B*0801 | B*1501 |
| 2 | IVLTQSPGT | 1 | 22 | 1 | 1 | 11 | 1 | 2 | 0 |
| 3 | VLTQSPGTL | 0 | 23 | 2 | 0 | 18 | 0 | 1 | 0 |
| 5 | TQSPGTLSF | 1 | 3 | 1 | 0 | 28 | 0 | 2 | 44 |
| 20 | TLSCRASQI | 1 | 28 | 2 | 2 | 14 | 3 | 8 | 1 |
| 25 | ASQIVSSSY | 5 | 5 | 2 | 9 | 13 | 6 | 2 | 49 |
| 26 | SQIVSSSYL | 1 | 24 | 4 | 3 | 16 | 10 | 3 | 19 |
| 28 | IVSSSYLAW | 0 | 6 | 4 | 3 | 34 | 5 | 2 | 0 |
| 29 | VSSSYLAWY | 44 | 4 | 2 | 9 | 12 | 1 | 1 | 2 |
| 32 | SYLAWYQQK | 0 | 10 | 23 | 28 | 29 | 4 | 1 | 0 |
| 33 | YLAWYQQKP | 0 | 41 | 4 | 2 | 14 | 6 | 2 | 2 |
| 40 | KPGQAPRLL | 0 | 2 | 2 | 0 | 7 | 29 | 1 | 0 |
| 42 | GQAPRLLIY | 0 | 10 | 10 | 7 | 12 | 6 | 2 | 49 |
| 46 | RLLIYGASS | 0 | 24 | 0 | 6 | 0 | 0 | 0 | 0 |
| 47 | LLIYGASSR | 0 | 33 | 4 | 85 | 5 | 4 | 1 | 6 |
| 48 | LIYGASSRA | 1 | 32 | 6 | 60 | 7 | 6 | 3 | 11 |
| 72 | FTLTISRLE | 4 | 22 | 2 | 4 | 18 | 11 | 6 | 3 |
| 78 | RLEPEDFAV | 1 | 19 | 2 | 2 | 7 | 4 | 0 | 2 |
| 86 | VYYCQQYGS | 1 | 1 | 0 | 1 | 21 | 5 | 0 | 1 |
| 90 | QQYGSSPRT | 1 | 12 | 3 | 11 | 6 | 7 | 1 | 24 |
| 91 | QYGSSPRTF | 1 | 0 | 1 | 1 | 65 | 6 | 1 | 2 |
| 95 | SPRTFGQGT | 1 | 0 | 2 | 0 | 12 | 41 | 2 | 2 |
| 97 | RTFGQGTKV | 1 | 30 | 37 | 15 | 8 | 1 | 2 | 4 |

EXAMPLE 6

Production of Recombinant Clonotypic Ig

In order to produce the recombinant clonotypic Ig VK3-20 and VK3-15 and to implement the production and purification process, these fragments derived from HCV-related lymphomas were inserted in the bacterial expression vector pET26b, suitable for production for clinical use.

The following operations were then performed:

insertion of the nucleotide sequences codified for VK3-20 and VK3-15 in the bacterial vector pET26b inoculation at a concentration of 1% of the total volume in SB culture medium buffered with 1% glucose fermentation for 8-12 hours at 37° C.

purification of the fragments.

In the fragment insertion passage the fragments are stably inserted in the kanamicin-resistant bacterial expression vector pET26b, and produced fragments are identified and quantified with monoclonal antibodies (mAb) directed against the VK regions. In the inoculating passage a bacterial aliquote, pET26b/VK3-20/VK3-15, corresponding to 1% of the total volume, was inoculated in modified SB medium with the addition of phosphate buffer and with 1% glucose, induced with IPTG and kept in culture overnight at a temperature of 37° C., fermentation passage. The interesting fragments were purified in the purification passage both by the culture medium and by the bacterial periplasmic space. The process contemplates the passage of the extract and of the medium on an ion exchange resin Q Sepharose FF (Amersham-GE) to bond the reject products, while the interesting fragments VK3-20 and VK3-15 are collected as elution products of the column and further processed on cation exchange resin S Sepharose FF (Amersham-GE). The purity of the VK3-20 and VK3-15 fragments was assessed with SDS-PAGE analyses. The process described above allowed, within tolerant limits, the purification of about 37 mg of fragment with a yield of 4 mg/L from periplasmic extract and of 30 mg from culture medium with a yield of 20 mg/L.

EXAMPLE 7

Cross-Reactive Citotoxic Response Against Similar Epitopes Belonging to not Related VK-Protein Induced by Specific Peptide CTL VK3-20

The observation that specific CTL VK3-20 can induce cross-reactive citotoxic response against VK3-15, suggested the hypothesis that VK3-20 could contain potentially cross-reactive immunogenic epitopes against similar peptides belonging also to the light chain of VK-III family or other family. Therefore, an immunoinformatic analysis has been conducted aligning the sequences of the epitopes T HLA-A*0201 of VK3-20 against the sequences of all the VK chains collected by ImMunoGeneTics information System®.

As conservative attitude, only peptides with a single amino acid variation were took in account. The analysis conducted seems to suggest an high conservation grade of the epitopes VK3-20 within the VK-III family. For peptide P20 two potentially cross-reactive epitopes belonging to other proteins of the VK-III family were identified (table 2).

TABLE 2

HLA-A*0201cross-reactive peptide compared to P20 peptide (VK3-20) (SEQ ID NO: 6) and VK derived chain (Table 2 also discloses SEQ ID NOS 25-26, respectively, in order of appearance).

| No. peptide | Sequence peptide | VK derived chain |
|---|---|---|
| "Native peptide" | | |
| P20 "cross-reactive" peptide | TLSCRASQI | VK3-20 |
| H (9S) | TLSCRASQS | VK3-7; VK3D-7; VK3-11; VK3-15; VK3D-15; VK3-20 |
| H (9G) | TLSCRASQG | VK3D-11 |

It is interesting to point out how to the epitope P33 of VK3-20 corresponds some analogue epitopes potentially cross-reactive belonging to VK proteins of other families (VK-1, VK-V and VK-V1) (Table 3), furthermore, those are not infrequently expressed in lymphoid tumours.

TABLE 3

HLA-A*0201 cross-reactive peptide compared to P33 peptide (VK3-20) (SEQ ID NO: 27) and VK derived chain (Table 3 also discloses SEQ ID NOS 28-34, respectively, in order of appearance).

| No. peptide | Sequence peptide | VK derived chain |
|---|---|---|
| "Native peptide" | | |
| P33 | YLAWYQQKR | VK3-20 |
| "cross-reactive" peptide | | |
| H (3T) | YLTWYQQKR | VK3-7 |
| H (5F) | YLAWFQQKR | VK1-16; VK1D-13 |
| H (3S) | YLSWYQQKR | VK3D-7 |
| H (1W) | WLAWYQQKR | VK1-5; VK1-12; VK1D-12; VK1D-16 |
| H (1A) | ALAWYQQKR | VK1-13*02; VK1D-13 |
| H (3Y) | YLYWYQQKR | VK6D-41 |
| H (3N) | YLNWYQQKR | VK1-33; VK1D-33; VK1-39; VK1D-39; VK3-15; VK3D-15 |

To demonstrate the real effectiveness of that cross-reactivity, two CTL lines were obtained from 2 HLA-A*0201 donors specific for the peptides P20 and P33 of VK3-20. The lines obtained were able to lysate in a specific manner and HLA-A2-restricted autologue lymphoblastoid lines pulsed with the inducer peptide or with the entire VK3-20, and the lines DG75 (VK3-20+) and SH9 (VK3-15+) (FIG. 7). Those results further support that the immunogenicity of the protein Vk3-20 and indicate at the same time that is relative easy obtain ex-vivo CTL specific against the epitopes HLA-A*0201 of VK3-20 starting from mononucleate cells from the peripheral blood of healthy donors. The CTL lines obtained in this way were later analyzed for the capacity to lysate autologue targets (LCLs) alternatively presenting the inducer peptide and a series of "cross-reactive" peptides belonging to different VK proteins (Table 2 and 3). The analysis demonstrate that the CTL lines specific against P20 or P33 are able to exert ah high citotoxicity HLA-A*0201-restricted toward all the "cross-reactive" peptides studied (FIGS. 8 and 9).

The analysis of peptide-specific CTL obtained from 2 different donors allowed to obtain comparable results against all the "cross-reactive" peptides HLA-A*0201 investigated.

The data obtained support the conclusion that the protein VK3-20 could be considered a "carrier" of numerous immunogenic epitopes presented by the most common HLA class I. Those epitopes, naturally presented by the lymphoma VK3-20+ cells can mediate immune response that are very likely to be effective not only against lymphomes expressing light chains of the VK-III family, but also toward lymphomes expressing VK proteins of different families. Those results provide so a solid pre-clinic rationale to develop recombinant vaccines based on the usage of Id shared between different B-cell lymphoproliferations for a "cross-reactive" immunotherapy.

EXAMPLE 8

Production of the Protein VK3-20 in Bioreactor Wave

In order to have a production process for the protein VK3-20 that could be quickly transferred in a GMP contest, a procedure for fermentation in the disposable bioreactor Wave EHTD 20/50 (GE Healthcare) has been developed. This tool uses sterile and disposable bags and therefore allows, compared with traditional fermenters, to eliminate the risk of cross-contamination between different batch. For the same reason there is no need of validation procedures for cleaning and sterilization.

Fermentation was performed according to the following Protocol:

Preculture Preparation:

A single bag is attached to the oscillating plane of bioreactor and filled in sterile condition with 100 ml of SBT medium. 50 µl of bacteria from the glycerol stock are taken and pipetted in 1 ml of SBT medium which is then inoculated into the bag through a syringe. The preculture is kept overnight at 37° C. shaking, setting the bioreactor with a swing of 12° and a speed of 40 rpm.

Fermentation:

The day after a new disposable bag is prepared by filling it with 10 L of SBT medium. 100 ml of preculture are inoculated in 10 L of medium using the tubes with luer junction equipped on the bags. The culture is then fermented for 3 hours at 37° C., shaking (12°, 40 rpm). After 3 hours the inducer, IPTG, is added to the culture using a syringe at a final concentration of 1 mM and the culture then proceed growing overnight at the same conditions of temperature and shaking.

The monitoring of bacterial growth through reading of optical density at 600 nm gave the following results:

| Time (minutes) | Absorbancy 600 nm |
|---|---|
| 0 | 0.168 |
| 58 | 0.39 |
| 83 | 0.697 |
| 90 | 0.806 |
| 97 | 0.989 |
| 157 | 1.52 |
| 277 | 2.1 |
| 337 | 2.33 |
| 397 | 2.98 |
| 1440 | 5.86 |

These data indicate that the growth of bacterial population in the bioreactor Wave follows a trend comparable to what obtains in a classical system (shake flask).

The biomass obtained from the fermentation process was on average 18 grams of pellets per liter of bacterial culture and the production of protein VK3-20 was comparable to that achieved in accordance with the procedures of traditional fermentation.

Therefore it is possible to generate a reproducible and ideal process suitable for GMP production using the bioreactor Wave for fermentation. The bioreactor also allows a linear scale-up process up to 500 L, and so it is able to generate enough material to support clinical stages.

EXAMPLE 9

Conjugation Protein VK3-20 with KLH

To enhance the immunogenic properties of the VK3-20 protein a procedure for conjugation of polypeptide with Hemocyanin (Keyhole Limpet Hemocyanin, KLH, Vacmune) was developed. The conjugated protein is used in immunization protocols for the generation of monoclonal antibodies.

The purified protein is conjugated to KLH according to the following protocol.

A solution of Sulfo SMCC in PBS is prepared at the concentration of 4.8 mg/ml. 260 µl of KLH stock solution (concentrate 20 mg/ml) are taken and added to 44 µl of the prepared Sulfo SMCC solution, plus 200 µl of PBS: the mixture is then incubated for 30 minutes at room temperature. The excess of crosslinker is removed using a Centricon (50 KDa cut-off, Millipore). To the solution prepared 6 mg of protein VK3-20 previously purified and dialized in PBS are added and then incubated for 30 minutes at room temperature. The efficiency of the conjugation process is assessed by quantifying the protein content in the flow through and the retenate after filtration of the final product on a membrane with a 50 KDa cut-off.

The invention claimed is:

1. An immunogenic composition for an HCV-related or nonHCV-related lymphoproliferative pathology, the composition comprising at least one recombinant protein segment chosen between VK3-20 (SEQ ID NO: 35) and VK3-15 (SEQ ID NO: 36).

2. The composition according to claim 1 comprising both the recombinant protein segments VK3-20 and VK3-15.

3. A method for immunization against lymphoproliferative pathologies comprising the step of administering a composition comprising at least one recombinant protein segment selected from the group consisting of VK3-20 (SEQ ID NO: 35), VK3-15 (SEQ ID NO: 36), VK3-20 and VK3-15, and mixtures of the same to a patient in need thereof.

4. A method for immunization against HCV-related and nonHCV-related lymphoproliferative pathologies comprising the step of administering a composition of claim 1 to a patient in need thereof.

5. An immunogenic composition for immunization against lymphoproliferations which comprises at least one recombinant protein segment chosen between VK3-20 (SEQ ID NO: 35) and VK3-15(SEQ ID NO: 36), in a mixture with at least one pharmaceutically acceptable excipient.

6. The composition according to claim 5 which comprises both the recombinant protein segments VK3-20 and VK3-15.

7. The composition according to claim 5 for oral, parenteral or topic administration, which is from 0.1 to 1 mg of the recombinant protein segment.

8. A process for production of at least one recombinant protein segment chosen between VK3-20 (SEQ ID NO: 35) and VK3-15 (SEQ ID NO: 36) which comprises insertion of a nucleotide sequence encoding the recombinant protein segment in a suitable expression vector, fermentation, isolation and purification of said recombinant protein segment.

9. The process according to claim 8, wherein said nucleotide sequence is inserted in a kanamicin-resistant bacterial expression vector pET26b to form recombinant bacterial strain pET26b/VK3-20/VK3-15.

10. The process according to claim 8, wherein said at least one recombinant protein segment chosen between VK3-20 and VK3-15 is identified and quantified with mAb anti-VK.

11. The process according to claim 9, wherein said fermentation comprises inoculation of 1% of said recombinant bacterial strain pET26b/VK3-20/VK3-15 in SB medium.

12. The process according to claim 11, wherein said SB medium is buffered.

13. The process according to claim 12, wherein said medium is buffered with phosphate buffer and contains 1% (w/w) glucose.

14. The process according to claim 11, wherein said recombinant bacterial strain is kept in culture at 37° C. for 8-12 hours.

15. The process according to claim 8, wherein said at least one recombinant protein segment chosen between VK3-20 and VK3-15 is isolated either from culture medium or bacterial periplasmic space by elution on ion exchange resin Q Sepharose FF (Amersham-GE).

16. The process according to claim 15, wherein eluate is purified on cation exchange resin S Sepharose FF (Amersham-GE).

17. The composition of claim 5 further comprising sargramostim and/or recombinant IFN-α2a.

18. The composition of claim 5, which is 0.5 mg of recombinant protein segment, and further comprising sargramostim GM-CSF at 50 µg/m²/dose.

19. The composition of claim 5, which is 0.5 mg of recombinant protein segment, and further comprising recombinant IFN-α2a at 1,000,000 UI/m²/dose.

20. The composition of claim 5, which is 0.5 mg of recombinant protein segment, and further comprising sargramostim GM-CSF at 50 µg/m²/dose and recombinant IFN-α2a at 1,000,000 UI/m²/dose.

21. The method of claim 4, wherein the HCV-related lymphoproliferative pathology is selected from the group consisting of B-cell non-Hodgkin lymphoma, hepatocellular carcinoma, and thyroid cancer, wherein the non-HCV-related lymphoproliferative pathology is selected from the group consisting of follicular lymphoma (FL), chronic lymphocyte leukemia (CLL), lymphoma of mucosa-associated lymphoid tissue (MALT), lymphoma associated with rheumatoid arthritis, and lymphoma associated with Sjögren's syndrome.

* * * * *

UNITED STATES PATENT AND TRADEMARK OFFICE
CERTIFICATE OF CORRECTION

PATENT NO.       : 8,512,703 B2
APPLICATION NO.  : 12/670949
DATED            : August 20, 2013
INVENTOR(S)      : Dolcetti et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 609 days.

Signed and Sealed this
Fifteenth Day of September, 2015

Michelle K. Lee
*Director of the United States Patent and Trademark Office*

SEQUENCE LISTING

<160> NUMBER OF SEQ ID NOS: 36

<210> SEQ ID NO 1
<211> LENGTH: 24
<212> TYPE: DNA
<213> ORGANISM: Artificial Sequence
<220> FEATURE:
<223> OTHER INFORMATION: Synthetic primer

<400> SEQUENCE: 1
cgggatccgg aaattgtgtt gacg                      24

```
<210> SEQ ID NO 2
<211> LENGTH: 25
<212> TYPE: DNA
<213> ORGANISM: Artificial Sequence
<220> FEATURE:
<223> OTHER INFORMATION: Synthetic primer

<400> SEQUENCE: 2
ccgctcgagt catttgattt ccacc                                       25

<210> SEQ ID NO 3
<211> LENGTH: 9
<212> TYPE: PRT
<213> ORGANISM: Homo sapiens

<400> SEQUENCE: 3

Ile Val Leu Thr Gln Ser Pro Gly Thr
1               5

<210> SEQ ID NO 4
<211> LENGTH: 9
<212> TYPE: PRT
<213> ORGANISM: Homo sapiens

<400> SEQUENCE: 4

Val Leu Thr Gln Ser Pro Gly Thr Leu
1               5

<210> SEQ ID NO 5
<211> LENGTH: 9
<212> TYPE: PRT
<213> ORGANISM: Homo sapiens

<400> SEQUENCE: 5

Thr Gln Ser Pro Gly Thr Leu Ser Phe
1               5

<210> SEQ ID NO 6
<211> LENGTH: 9
<212> TYPE: PRT
<213> ORGANISM: Homo sapiens

<400> SEQUENCE: 6

Thr Leu Ser Cys Arg Ala Ser Gln Ile
1               5

<210> SEQ ID NO 7
<211> LENGTH: 9
<212> TYPE: PRT
<213> ORGANISM: Homo sapiens

<400> SEQUENCE: 7

Ala Ser Gln Ile Val Ser Ser Ser Tyr
1               5

<210> SEQ ID NO 8
<211> LENGTH: 9
<212> TYPE: PRT
<213> ORGANISM: Homo sapiens

<400> SEQUENCE: 8

Ser Gln Ile Val Ser Ser Ser Tyr Leu
1               5

<210> SEQ ID NO 9
```

```
<211> LENGTH: 9
<212> TYPE: PRT
<213> ORGANISM: Homo sapiens

<400> SEQUENCE: 9

Ile Val Ser Ser Ser Tyr Leu Ala Trp
1               5

<210> SEQ ID NO 10
<211> LENGTH: 9
<212> TYPE: PRT
<213> ORGANISM: Homo sapiens

<400> SEQUENCE: 10

Val Ser Ser Ser Tyr Leu Ala Trp Tyr
1               5

<210> SEQ ID NO 11
<211> LENGTH: 9
<212> TYPE: PRT
<213> ORGANISM: Homo sapiens

<400> SEQUENCE: 11

Ser Tyr Leu Ala Trp Tyr Gln Gln Lys
1               5

<210> SEQ ID NO 12
<211> LENGTH: 9
<212> TYPE: PRT
<213> ORGANISM: Homo sapiens

<400> SEQUENCE: 12

Tyr Leu Ala Trp Tyr Gln Gln Lys Pro
1               5

<210> SEQ ID NO 13
<211> LENGTH: 9
<212> TYPE: PRT
<213> ORGANISM: Homo sapiens

<400> SEQUENCE: 13

Lys Pro Gly Gln Ala Pro Arg Leu Leu
1               5

<210> SEQ ID NO 14
<211> LENGTH: 9
<212> TYPE: PRT
<213> ORGANISM: Homo sapiens

<400> SEQUENCE: 14

Gly Gln Ala Pro Arg Leu Leu Ile Tyr
1               5

<210> SEQ ID NO 15
<211> LENGTH: 9
<212> TYPE: PRT
<213> ORGANISM: Homo sapiens

<400> SEQUENCE: 15

Arg Leu Leu Ile Tyr Gly Ala Ser Ser
1               5

<210> SEQ ID NO 16
<211> LENGTH: 9
<212> TYPE: PRT
<213> ORGANISM: Homo sapiens
```

```
<400> SEQUENCE: 16

Leu Leu Ile Tyr Gly Ala Ser Ser Arg
1               5

<210> SEQ ID NO 17
<211> LENGTH: 9
<212> TYPE: PRT
<213> ORGANISM: Homo sapiens

<400> SEQUENCE: 17

Leu Ile Tyr Gly Ala Ser Ser Arg Ala
1               5

<210> SEQ ID NO 18
<211> LENGTH: 9
<212> TYPE: PRT
<213> ORGANISM: Homo sapiens

<400> SEQUENCE: 18

Phe Thr Leu Thr Ile Ser Arg Leu Glu
1               5

<210> SEQ ID NO 19
<211> LENGTH: 9
<212> TYPE: PRT
<213> ORGANISM: Homo sapiens

<400> SEQUENCE: 19

Arg Leu Glu Pro Glu Asp Phe Ala Val
1               5

<210> SEQ ID NO 20
<211> LENGTH: 9
<212> TYPE: PRT
<213> ORGANISM: Homo sapiens

<400> SEQUENCE: 20

Val Tyr Tyr Cys Gln Gln Tyr Gly Ser
1               5

<210> SEQ ID NO 21
<211> LENGTH: 9
<212> TYPE: PRT
<213> ORGANISM: Homo sapiens

<400> SEQUENCE: 21

Gln Gln Tyr Gly Ser Ser Pro Arg Thr
1               5

<210> SEQ ID NO 22
<211> LENGTH: 9
<212> TYPE: PRT
<213> ORGANISM: Homo sapiens

<400> SEQUENCE: 22

Gln Tyr Gly Ser Ser Pro Arg Thr Phe
1               5

<210> SEQ ID NO 23
<211> LENGTH: 9
<212> TYPE: PRT
<213> ORGANISM: Homo sapiens

<400> SEQUENCE: 23
```

Ser Pro Arg Thr Phe Gly Gln Gly Thr
1               5

<210> SEQ ID NO 24
<211> LENGTH: 9
<212> TYPE: PRT
<213> ORGANISM: Homo sapiens

<400> SEQUENCE: 24

Arg Thr Phe Gly Gln Gly Thr Lys Val
1               5

<210> SEQ ID NO 25
<211> LENGTH: 9
<212> TYPE: PRT
<213> ORGANISM: Homo sapiens

<400> SEQUENCE: 25

Thr Leu Ser Cys Arg Ala Ser Gln Ser
1               5

<210> SEQ ID NO 26
<211> LENGTH: 9
<212> TYPE: PRT
<213> ORGANISM: Homo sapiens

<400> SEQUENCE: 26

Thr Leu Ser Cys Arg Ala Ser Gln Gly
1               5

<210> SEQ ID NO 27
<211> LENGTH: 9
<212> TYPE: PRT
<213> ORGANISM: Homo sapiens

<400> SEQUENCE: 27

Tyr Leu Ala Trp Tyr Gln Gln Lys Arg
1               5

<210> SEQ ID NO 28
<211> LENGTH: 9
<212> TYPE: PRT
<213> ORGANISM: Homo sapiens

<400> SEQUENCE: 28

Tyr Leu Thr Trp Tyr Gln Gln Lys Arg
1               5

<210> SEQ ID NO 29
<211> LENGTH: 9
<212> TYPE: PRT
<213> ORGANISM: Homo sapiens

<400> SEQUENCE: 29

Tyr Leu Ala Trp Phe Gln Gln Lys Arg
1               5

<210> SEQ ID NO 30
<211> LENGTH: 9
<212> TYPE: PRT
<213> ORGANISM: Homo sapiens

<400> SEQUENCE: 30

Tyr Leu Ser Trp Tyr Gln Gln Lys Arg
1               5

<210> SEQ ID NO 31
<211> LENGTH: 9
<212> TYPE: PRT
<213> ORGANISM: Homo sapiens

<400> SEQUENCE: 31

Trp Leu Ala Trp Tyr Gln Gln Lys Arg
1               5

<210> SEQ ID NO 32
<211> LENGTH: 9
<212> TYPE: PRT
<213> ORGANISM: Homo sapiens

<400> SEQUENCE: 32

Ala Leu Ala Trp Tyr Gln Gln Lys Arg
1               5

<210> SEQ ID NO 33
<211> LENGTH: 9
<212> TYPE: PRT
<213> ORGANISM: Homo sapiens

<400> SEQUENCE: 33

Tyr Leu Tyr Trp Tyr Gln Gln Lys Arg
1               5

<210> SEQ ID NO 34
<211> LENGTH: 9
<212> TYPE: PRT
<213> ORGANISM: Homo sapiens

<400> SEQUENCE: 34

Tyr Leu Asn Trp Tyr Gln Gln Lys Arg
1               5

<210> SEQ ID NO 35
<211> LENGTH: 84
<212> TYPE: PRT
<213> ORGANISM: Homo sapiens

<400> SEQUENCE: 35

Ser Gln Ile Val Ser Ser Tyr Leu Ala Trp Tyr Gln Gln Lys Pro
1               5                   10                  15

Gly Gln Ala Pro Arg Leu Leu Ile Tyr Gly Ala Ser Ser Arg Ala Thr
            20                  25                  30

Gly Ile Pro Asp Arg Phe Ser Gly Ser Gly Ser Gly Thr Asp Phe Thr
        35                  40                  45

Leu Thr Ile Ser Arg Leu Lys Pro Glu Asp Phe Ala Val Tyr Tyr Cys
    50                  55                  60

Gln Gln Tyr Gly Ser Ser Pro Arg Thr Phe Gly Gln Gly Thr Lys Leu
65                  70                  75                  80

Gly Asn Gln Thr

<210> SEQ ID NO 36
<211> LENGTH: 108
<212> TYPE: PRT
<213> ORGANISM: Homo sapiens

<400> SEQUENCE: 36

Glu Ile Val Met Thr Gln Ser Pro Ala Thr Leu Ser Val Ser Pro Gly
1               5                   10                  15

```
Glu Arg Ala Thr Leu Ser Cys Arg Ala Ser Gln Ser Val Ser Ser Asn
            20                  25                  30

Leu Ala Trp Tyr Gln Gln Pro Gly Gln Ala Pro Arg Leu Leu Ile
        35                  40                  45

Tyr Gly Ala Ser Thr Arg Ala Thr Gly Ile Pro Ala Arg Phe Ser Gly
        50                  55                  60

Ser Gly Ser Gly Thr Glu Phe Thr Leu Thr Ile Asn Ser Leu Gln Ser
65                  70                  75                  80

Glu Asp Phe Ala Val Tyr Tyr Cys Gln Gln Tyr Asn Asn Trp Pro Pro
                85                  90                  95

Trp Thr Phe Gly Gln Gly Thr Lys Val Glu Ile Lys
            100                 105
```